United States Patent [19]

Baker et al.

[11] Patent Number: 4,845,110
[45] Date of Patent: Jul. 4, 1989

[54] ORGANIC COMPOUNDS AND THEIR PHARMACEUTICAL USE

[75] Inventors: Stephen R. Baker, Camberley; Alec Todd, Wokingham, both of England

[73] Assignee: Lilly Industries Limited, London, United Kingdom

[21] Appl. No.: 938,177

[22] Filed: Dec. 4, 1986

[30] Foreign Application Priority Data

Dec. 7, 1985 [GB] United Kingdom ............... 8530222

[51] Int. Cl.$^4$ .................... C07D 257/04; A61K 31/41
[52] U.S. Cl. .................... 514/381; 548/253; 558/396; 558/397; 558/413; 558/414; 562/480; 562/452; 564/161; 564/163
[58] Field of Search ............... 548/253; 514/381

[56] References Cited

FOREIGN PATENT DOCUMENTS 2144422 3/1985 United Kingdom.
2168704 6/1986 United Kingdom.
2170204 7/1986 United Kingdom.

OTHER PUBLICATIONS

Bohlmann et al., *Chem. Ber.*, 98(9), 3015 (1965).
Jonczyk et al., *J. Org. Chem.*, 48, 910 (1983).
Knochel et al., *Tetrahedron Letters*, 26, 425 (1985).
Labidalle et al., *Ann. Pharm. Fr.*, 39 (6), 545 (1981).
Van Tamelen et al., *J. Am. Chem. Soc.*, 103 (15), 4615 (1981).

*Primary Examiner*—David B. Springer
*Attorney, Agent, or Firm*—Robert A. Conrad; Leroy Whitaker

[57] ABSTRACT

There are provided anti-allergic pharmaceutical compounds of formula:

$$R^1\underset{(O)_n-SR^2}{\overset{1}{\underset{2}{\text{CH}}}}-\text{C}_6\text{H}_3(R^3)(R^4)(R^5) \quad (I)$$

in which n is 0, 1 or 2; $R^1$ is a hydrocarbyl group containing 6 to 30 carbon atoms and optionally substituted with an optionally substituted phenyl group; $R^2$ is (i) optionally optionally protected tetrazolyl, —COR$^6$ where $R^6$ is $C_{1-4}$alkyl, $C_{1-4}$alkoxy, an optionally protected amino acid residue or —NR$_2^7$ where each $R^7$ is hydrogen or $C_{1-4}$alkyl, and —NHR$^8$ where $R^8$ is hydrogen, a protecting group, an optionally protected amino acid residue, $C_{1-4}$alkyl or —COR$^9$ where $R^9$ is $C_{1-4}$alkyl or $C_{1-4}$alkoxy, or (iii) $C_{1-10}$alkyl substituted with a group selected from $$-\text{NH}-\underset{NR_2^{10}}{\overset{|}{\text{C}}}=\text{N}-\text{CN} \quad \text{and} \quad -\underset{CONR_2^{10}}{\overset{|}{\text{CH}}}-\text{NH}-\text{COR}^{10}$$

where each $R^{10}$ is hydrogen or $C_{1-4}$alkyl; and $R^3$, $R^4$ and $R^5$ are each selected from hydrogen, carboxyl, $C_{2-5}$alkoxycarbonyl, $C_{1-4}$alkyl, hydroxyl, optionally protected tetrazolyl, halo, trifluoromethyl, nitrile, nitro and —CONR$_2^{11}$ where each $R^{11}$ is hydrogen or $C_{1-4}$ alkyl; and salts thereof.

4 Claims, No Drawings

ORGANIC COMPOUNDS AND THEIR PHARMACEUTICAL USE

This invention relates to novel compounds and their use as pharmaceuticals.

In recent years a considerable effort has been invested in research into leukotrienes, the mediators in a variety of cell functions. Most workers in this field whose research has been based on the naturally-occurring leukotrienes have retained the neighbouring hydroxy and sulphur substituents as essential features of the chemical structure.

In contrast, the compounds of the invention are desoxy derivatives and lack the hydroxy substituent on the hydrocarbyl chain. They have the general formula:

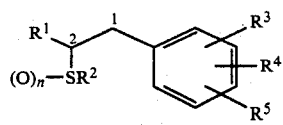
(I)

in which n is 0, 1 or 2; $R^1$ is a hydrocarbyl group containing 6 to 30 carbon atoms and optionally substituted with an optionally substituted phenyl group; $R^2$ is (i) optionally substituted phenyl, (ii) $C_{1-10}$alkyl optionally substituted with one or more substituents selected from optionally protected hydroxyl, optionally protected carboxyl, nitrile, optionally protected tetrazolyl, —$COR^6$ where $R^6$ is $C_{1-4}$alkyl, $C_{1-4}$alkoxy, an optionally protected amino acid residue or —$NR_2^7$ where each $R^7$ is hydrogen or $C_{1-4}$alkyl, and -$NHR^8$ where $R^8$ is hydrogen, a protecting group, an optionally protected amino acid residue, $C_{1-4}$alkyl or —$COR^9$ where $R^9$ is $C_{1-4}$alkyl or $C_{1-4}$alkoxy, or (iii) $C_{1-10}$alkyl substituted with a group selected from

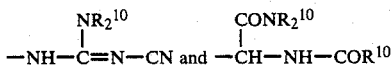

where each $R^{10}$ is hydrogen or $C_{1-4}$alkyl; and $R^3$, $R^4$ and $R^5$ are each selected from hydrogen, carboxyl, $C_{2-5}$alkoxycarbonyl, $C_{1-4}$alkyl, $C_{1-4}$alkoxy, hydroxyl, optionally protected tetrazolyl, halo, trifluoromethyl, nitrile, nitro and —$CONR_2^{11}$ where each $R^{11}$ is hydrogen or $C_{1-4}$alkyl; and salts thereof.

The compounds of the invention, in unprotected form, have been shown to be pharmacologically active in tests which demonstrate their antagonist effect on leukotriene receptors and indicate their use in the treatment of allergic disorders.

In the above general formula, the hydrocarbyl group preferably contains from 6 to 30 carbon atoms and includes alkyl, alkenyl and alkynyl groups. Such substituents can be substituted with a phenyl or a substituted phenyl group. The hydrocarbyl group preferably contains from 6 to 20 carbon atoms, for example from 10 to 20 carbon atoms and especially from 10 to 15 carbon atoms. When $R^1$ is alkyl it can be branched or unbranched and is preferably one containing 10 to 15 carbon atoms. When $R^1$ is alkenyl it can be branched or unbranched preferably containing 10 to 15 carbon atoms, such as for example 12 to 15. The alkenyl group preferably contains 1 to 4 double bonds and can be, for example, of the general formula

where $R^{12}$ is $C_{7-11}$alkyl or $CH_3(CH_2)_nCH$=$CH$—$CH_2$—$CH$=$CH$— where n is 0 to 4. It will be appreciated that such double bonds provide opportunities for cis-trans isomeric forms. Two examples of alkenyl groups are:

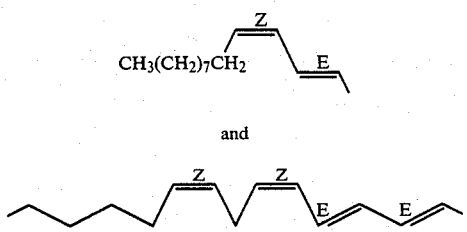

When $R^1$ is alkynyl it can be branched or unbranched, and preferably contains from 10 to 15 carbon atoms having 1 to 4 triple bonds. It is to be understood that such alkynyl groups can also contain one or more, for example, 1 to 3 double bonds in addition to its triple bond or bonds.

When $R^1$ is substituted hydrocarbyl it is substituted by an optionally substituted phenyl ring, preferably phenyl itself, or a phenyl group substituted with one or more, preferably 1 to 3, substituents selected from $C_{1-4}$alkyl, especially methyl, $C_{1-4}$alkoxy, especially methoxy and ethoxy, hydroxy, nitro, cyano, halo, especially chloro, trifluoromethyl, carboxyl, tetrazolyl and —$CONH_2$. When $R^1$ is substituted it is preferably an alkenyl group and a preferred value is the terminally substituted ω-phenyl alkenyl group.

It is preferred that $R^1$ is one of the above defined alkenyl groups.

With regard to $R^2$, this can be a $C_{1-10}$alkyl group, preferably $C_{1-6}$alkyl, and optionally substituted by one or more, preferably 1 to 3, substituents as defined above. The substituent can be —$COR^6$ or —$NHR^8$ where $R^6$ and $R^8$ are amino acid residue. Such amino acid residues can be optionally protected by a conventional protecting group and can be derived from any of the commonly occurring amino acids. In the case of $R^6$ the residue is preferably derived from glycine having the value —$NHCH_2COOH$ and in the case of $R^8$ it is preferably derived from aspartic acid or glutamic acid, having the values —$COCH_2CH(NH_2)COOH$ and —$COCH_2CH_2CH(NH_2)COOH$, respectively. Examples of the $SR^2$ group include cysteinyl, cysteinylglycinyl and glutathionyl of formulae

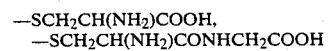

and

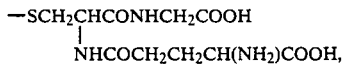

respectively.

Preferably $R^2$ is an alkyl group substituted with 1 to 3 substituents selected from carboxyl, nitrile, tetrazolyl, and —$COR^6$ where $R^6$ is —$NR_2^7$ or $C_{1-4}$alkoxy.

A preferred value of $R^2$ is of the following formula:

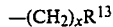

where x is 1 to 5 and $R^{13}$ is carboxyl, nitril, -$CONH_2$ or tetrazolyl. Most preferred are groups in which x is 2 and/or $R^{13}$ is carboxyl or tetrazolyl.

As mentioned above, $R^2$ can be optionally substituted phenyl and it can be any of the values defined above when $R^1$ bears an optionally substituted phenyl group. Preferably the phenyl ring is substituted with 1 to 3 substituents selected from carboxyl, tetrazolyl and —$CONH_2$, and especially a single carboxyl substituent.

As defined above, the groups $R^3$, $R^4$ and $R^5$ can be hydrogen, carboxyl, $C_{2-5}$alkoxycarbonyl, $C_{1-4}$alkyl, $C_{1-4}$alkoxy, hydroxyl, optionally protected tetrazolyl, halo, trifluoromethyl, nitrile, nitro and —$CONR_2^{11}$ where each $R^{11}$ is hydrogen or $C_{1-4}$alkyl. The tetrazolyl group is preferably 1H-tetrazol-5-yl. Preferably there is a single substituent on the phenyl ring and it is preferred that the substituent be nitrile, —$CONH_2$, tetrazolyl or carboxyl, acid substituents such as tetrazolyl and carboxyl being best of all. Maximum biological activity is given by the compounds in which the tetrazolyl or carboxyl group is attached at the ortho or meta positions, and the most preferred groups are of the formula

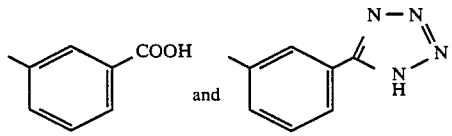

Preferred compounds of formula (I) above are those in which n is 0.

In the above general formulae $C_{1-4}$alkyl means a straight or branched chain alkyl group, for example, methyl, ethyl, propyl, isopropyl, butyl, isobutyl and tertiary butyl, and is preferably methyl or ethyl. Similarly a $C_{1-4}$alkoxy group is any such alkyl group attached through oxygen to the appropriate moiety, and alkoxycarbonyl is a group of the form ROCO— where R is a $C_{1-4}$alkyl group as described above.

A preferred group of compounds is one of formula (I) above in which n is 0, $R^1$ is $R^{12}CH=CHCH=CH—$ where $R^{12}$ is $C_{7-11}$alkyl, $R^2$ is —$(CH_2)_xR^{13}$ where x is 1 to 5 and $R^{13}$ is carboxyl, nitrile, —$CONH_2$ or tetrazolyl, $R^3$ is carboxyl or tetrazolyl and $R^4$ and $R^5$ are both hydrogen, and salts thereof.

When substituents on the compound of formula (I) require protection during preparation they may be protected by conventional protecting groups. Compounds with such protected carboxyl, amino acid residues, amino, hydroxyl and tetrazolyl groups are included in the scope of the invention, though the preferred compounds with optimum biological properties are the unprotected compounds derived from them. Carboxy-protecting groups are the well known ester forming groups used for the temporary protection of acidic carboxylic acid groups. Examples of such groups which have general use are readily hydrolysable groups such as arylmethyl groups, haloalkyl groups, trialkylsilyl groups, alkyl groups, and alkenyl groups. Other carboxy protecting groups are those described by E. Haslam in Protective Groups in Organic Chemistry, Chapter 5. The amino-protecting groups that can be employed in the preparation of the compounds of the invention are also conventional protecting groups. Illustrative of such groups are trihaloacetyl groups especially trifluoroacetyl. Such groups are well known in the art and are discussed, for example, in Peptide Synthesis by M. Bodansky, Y. S. Klausner and M. A. Ondetti, Second Edition (1976) John Wiley & Sons. Any free hydroxy groups present in the compound of the invention may likewise be protected if needed. For example, a hydroxy group on the $R^2$ group of a compound of the formula I, can be protected with a conventional labile ether forming protecting group such as an ether formed with dihydropyran or methylvinyl ether, or by esters formed with the lower alkyl carboxylic acids such as formic, acetic or propionic, or such halogenated acids, for example, chloroacetic acid, dichloroacetic acid or $\beta,\beta$-dichloropropionic acid. Furthermore, it is usually necessary to protect any tetrazolyl group during the process of preparation, and suitable and well known protecting groups for this purpose include the trityl and benzhydryl groups formed by reaction with the appropriate halide in the presence of base for example by reacting the tetrazolyl reactant with trityl chloride and triethylamine. In addition substituted trityl, substituted benzhydryl and optionally substituted benzyl may also be used as tetrazolyl protecting groups. Such groups are substituted on the phenyl ring with substituents such as listed above as suitable for optionally substituted phenyl. Protecting groups for the tetrazolyl radical are discussed in Advances in Heterocyclic Chemistry, Academic Press, 1977, vol. 21, pages 323 to 435.

When the compound of formula (I) bears an acidic function, base addition salts can be prepared and these are to be regarded as part of the present invention. Examples of such salts are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, calcium hydroxide, methylamine, diethylamine, ethylene diamine, cyclohexylamine and ethanolamine. The potassium and sodium salt forms together with other pharmaceutically acceptable salts are particularly preferred, but it is to be understood that other non-pharmaceutical salts are included in the invention since they may be useful for identification, charactization or purification of the free compound.

When the compound of formula (I) has a basic function, acid addition salts can be prepared and these are included in the present invention. Example of such salts are those derived from, preferably non-toxic, inorganic acids such as for example hydrochloric acid, nitric acid, phosphoric acid, sulphuric acid and nitric acid, as well as salts derived from, preferably non-toxic, organic acids such as aliphatic mono- and di-carboxylic acids, phenyl-substituted alkanoic acid, hydroxyalkanoic acids, aromatic acids, and aliphatic and aromatic sulphonic acids.

It will be appreciated that compounds containing $R^1$ alkenyl substituents exhibit cis-trans isomeric forms. In addition the compounds of the invention possess a chiral centre at the main chain carbon atom to which the sulphur side chain is attached (position 2) and this results in R and S isomers and racemic mixtures. Such stereoisomers are included within the scope of the invention. Isomers can be isolated from racemic mixtures by conventional methods such as by the preparation of diastereoisomers with subsequent liberation of the enantiomers.

The invention also includes a process for producing a compound of formula (I), and salts thereof, which comprises reacting a compound of formula (II)

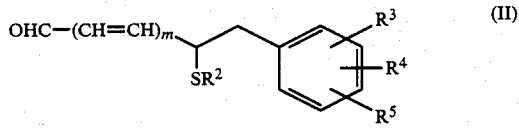

in which m is 0, 1, 2 or 3 and $R^2$, $R^3$, $R^4$ and $R^5$ are as defined for formula (I), such groups being protected when necessary, with a Wittig or Horner-Wittig reagent containing the moiety $RCH^\ominus$-$P^\oplus$ or

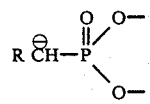

respectively, in which R is an appropriate hydrocarbyl group yielding an $R^1$ group having the required number of carbon atoms, and optionally when it is desired to prepare a compound of formula (I) in which n is 1 or 2, by oxidation, or when it is desired to prepared a compound of formula (I) in which $R^1$ in optionally substituted alkyl, by reduction, or by removal of a protecting group, or by interconversion of an $R^2$, $R^3$, $R^4$ or $R^5$ group.

The reaction of the aldehyde of formula (II) with Wittig reagent is preferably carried out in an inert solvent such as for example tetrahydrofuran, at a temperature of from $-100°$ C. to $20°$ C. In the case of reactants in which the $R^2$, $R^3$, $R^4$ or $R^5$ group is sensitive to the reaction, such groups should be suitably protected by a conventional protecting group which can subsequently be removed.

Preferred Wittig reagents are of the formula $RCH^\ominus$-$P^\oplus X_3$ where X is $C_{1-10}$ alkyl or phenyl optionally substituted with one or more, preferably 1 to 3, substituents selected from $C_{1-4}$ alkyl especially methyl, $C_{1-4}$ alkoxy especially methoxy, and halo especially chloro. Wittig reagents of the above formula are generally produced in situ by the reaction of a base with a phosphorus compound of the formula $RCH_2P^\oplus X_3Y$ where Y is halo especially bromo, or tosyl. The base can be, for example, butyl lithium or potassium t-butoxide.

Such Wittig reagents are readily prepared from halides or tosylates and substituted by conventional methods, and the R group is chosen such that the number of carbon atoms together with those contributed by the aldehyde side chain of the compound of formula (II), is such as to give an $R^1$ chain of the desired length. Thus R can be an appropriate alkyl, alkenyl or alkynyl group. It will be appreciated that the Wittig reagents can be replaced by Horner-Wittig phosphonate reagents of the formula

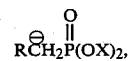

where X has the above defined values, and employed under similar conditions.

The compounds of formula (II) are novel and are included as part of the present invention. They can be prepared by a number of routes starting from compounds of the type

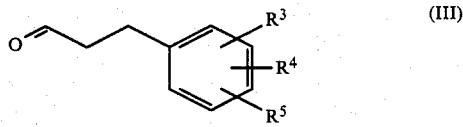

Compound (III) can be reacted with trimethyl silyl chloride and triethylamine in a solvent such as dimethylformamide so as to form the enol ether derivative:

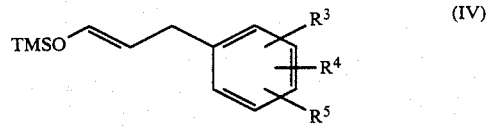

The compound of formula (IV) can be reacted with the appropriate sulphenyl halide, $R^2SCl$ (V), to give a compound of the formula

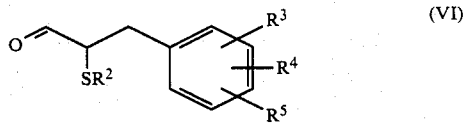

This is the compound of formula (II) above in which m is 0. Compound (VI) can be extended by reaction with the appropriate Wittig reagent of formula $Ph_3P$=(CH—CH=)$_x$CH—CHO where x is 0, 1 or 2.

Compounds of formula (III) are either known or can be prepared by conventional methods. For example the appropriate cinnamic acid derivative can be reduced with palladium and hydrogen to give the saturated side chain, followed by reduction with diborane to give the equivalent alcohol which in its turn can be oxidised using for example chromium trioxide to give the compound of formula (III). Alternatively the cinnamic acid derivative can be treated with oxalyl chloride followed by sodium borohydride on alumina, then by further reduction with palladium and hydrogen and oxidation with chromium trioxide. These reactions are summarised in the following scheme:

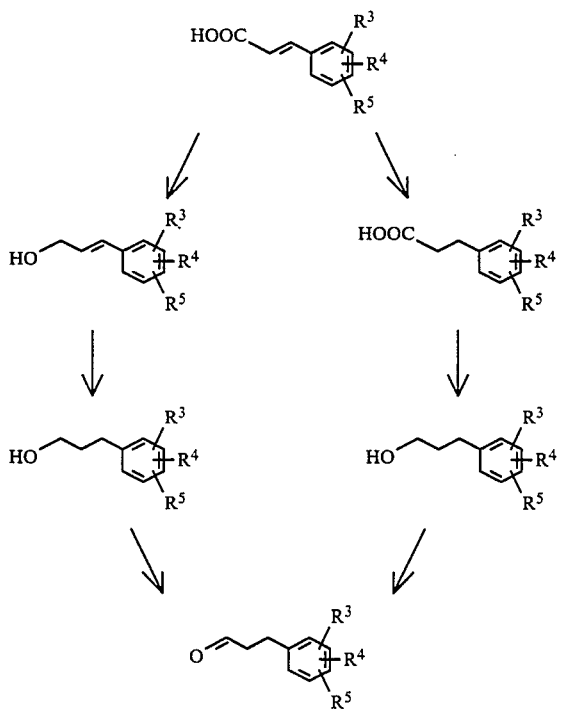

The sulphenyl reactants of formula (V) above can be prepared by chlorination of the appropriate disulphide. (Comprehensive Organic Chemistry Vol. 3., Ed. Sir Derek Barton, W. D. Ollis, p. 267.)

When it is desired to prepare the sulphoxide compounds in which n is 1 in formula (I) above, the corresponding sulphide in which n is 0 is reacted in substantially equivalent proportions with a suitable oxidising agent such as for example sodium periodate in an aqueous medium such as aqueous methanol at a temperature of, for example, from 0° C. to 50° C. The sulphone compounds in which n is 2 in formula (I) can be prepared by reacting the sulphide with an excess of oxidising agent such as for example potassium persulphate, or by reacting the appropriate sulphoxide with an excess of oxidising agent, both reactions being carried out under similar conditions to those employed in the preparation of the sulphoxide and preferably at a temperature of from 0° C. to 100° C.

It will be appreciated that it may be desired to remove any protecting groups attached to the product of the reaction. Such reactions can readily be carried out by use of a base in an inert organic solvent, such as for example, lithium hydroxide in tetrahydrofuran, or potassium carbonate in methanol, at a temperature of from 0° C. to 80° C., or by use of acid such as hydrochloric acid for removal of protecting groups from tetrazolyl, or by reduction in the case of protected amino groups, by well known procedures.

Also it will be appreciated that one or more of the substituents on the $R^2$ group or $R^3$, $R^4$ and $R^5$ groups can be interconverted. It is often preferred, depending on the nature of the group, that such interconversions are carried out after reaction of compound of formula (II) with Wittig reagent.

For example, compounds in which $R^3$, $R^4$ or $R^5$ is $C_{2-5}$alkoxycarbonyl or in which $R^2$ bears such a group can be converted to the corresponding free carboxyl by hydrolysis by means of base in an inert organic solvent, such as for example, lithium hydroxide in tetrahydrofuran. Such methods are well known in the art. Conversely, compounds in which $R^3$, $R^4$ or $R^5$ is $C_{2-5}$alkoxycarbonyl or $R^2$ has such a group can be prepared from the free acid by esterification of the free carboxyl group with the appropriate alcohol or by treatment with alkyl halide in the presence of base. Salts of the free acid can, of course, be prepared simply by reaction with alkali.

Compounds in which $R^3$, $R^4$ or $R^5$ is —$CONR_2^{11}$ or $R^2$ bears a —$CONR_2^7$ group can be prepared by reacting a compound with an appropriate alkoxycarbonyl substituent with ammonia or the appropriate amine of formula $R_2^{11}NH$ or $R_2^7NH$, respectively, or they can be prepared by the reaction of an amine of formula $R_2^{11}NH$ or $R_2^7NH$ with the appropriate acyl chloride, which can in its turn be derived from the free carboxyl derivative by the reaction of thionyl chloride. Such reactions are well known in the art.

Compounds in which $R^3$, $R^4$ or $R^5$ is a nitrile group or $R^2$ has such a group can be prepared by dehydration of the appropriate amide (—$CONH_2$), a convenient dehydrating agent being, for example, a mixture of triphenylphosphine and carbon tetrachloride.

Compounds in which $R^3$, $R^4$ or $R^5$ is tetrazolyl or $R^2$ has such a group can be prepared by reaction of the cyano derivative prepared as above with, for example sodium azide and ammonium chloride in dimethylformamide. Salts can be prepared from the tetrazolyl derivatives by the addition of base according to standard techniques.

It will be appreciated that the steps of reduction to provide the standard $R^1$ substituents, oxidation to provide sulphones and sulphoxides, removal of protecting group or interconversion of groups, can be carried out in whatever sequence best suits convenience and the aim of maximising yield.

Compounds of formula (I) in which $R^1$ is alkyl, that is, a saturated group can be prepared preferably by hydrogenation of the appropriate compound in which $R^1$ is alkenyl or alkynyl, with, for example, hydrogen and a heavy metal catalyst such as $PtO_2$ or Pd/carbon or other catalytic systems, preferably at a temperature of from 0° C. to 100° C. and in an organic solvent such as for example ethanol.

The following scheme gives an example of the way in which preferred compounds of the invention may be prepared:

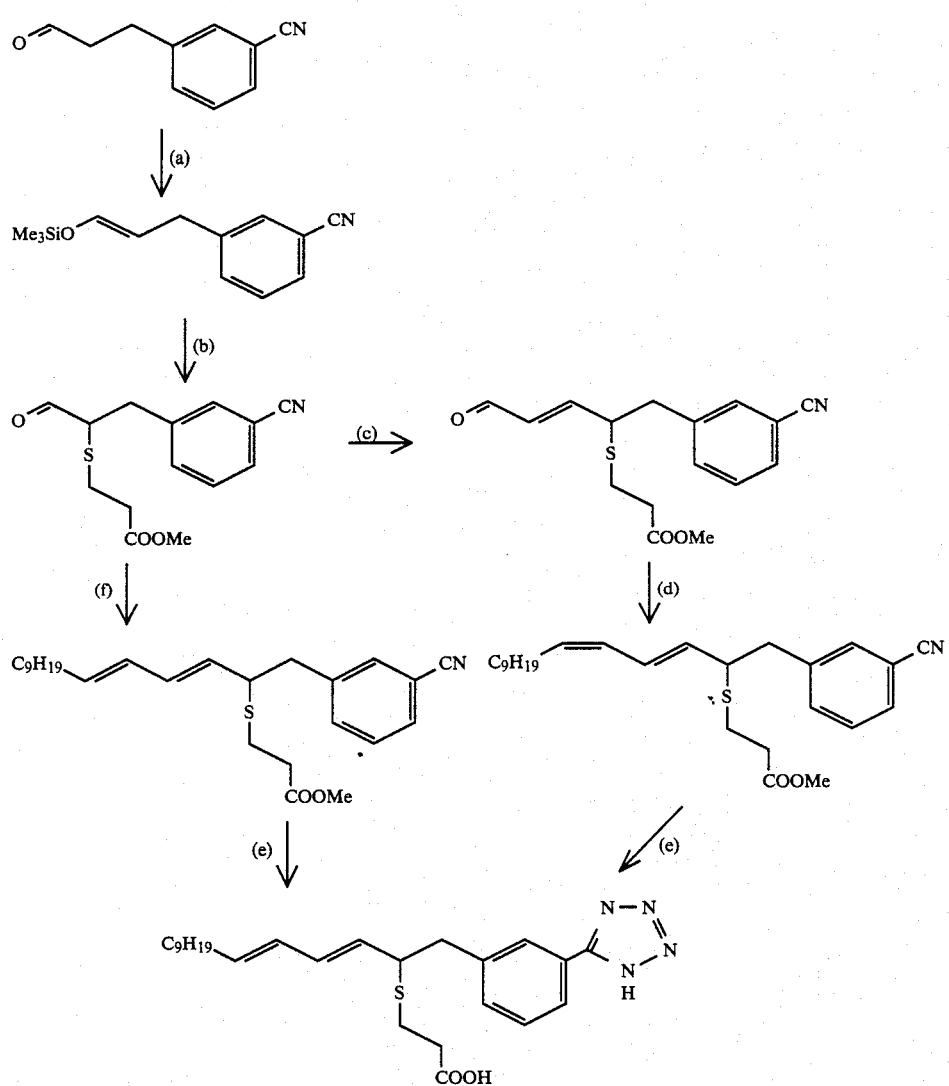

Key:
(a) Me₃SiCl/Et₃N/DMF
(b) ClSCH₂CH₂COOMe
(c) Ph₃P=CHCHO
(d) C₉H₁₉CH₂P⁺Ph₃Br⁻
(e) (i) K₂CO₃
    (ii) NaN₃/Et₃N.HCl (f) C₉H₁₉—CH=CH—CH₂—P⁺Ph₃Br⁻

The compounds of the present invention are pharmacologically active, being leukotriene antagonists as shown by the in vitro test on guinea pig ileum segments at concentrations of from 10 ng to 50 μg, according to the method of Schild (1947) Brit. J. Pharm. 2, 197–206 (the unprotected compounds of formula (I) described in the following Examples exhibited an $IC_{50}$ against $LTD_4$ of less than $10^{-5}$ molar). Also compounds of the invention are active in the in vivo Guinea Pig Pulmonary Function Test of Austen and Drazen (1974) J. Clin. Invest. 53 1679–1685 at intravenous dosage levels of from 0.05 μg to 5.0 mg/kg and in a modified "Herxheimer" test (Journal of Physiology (London) 117 251 (1952)) at doses of from 25 to 200 mg/kg. The "Herxheimer" test is based on an $LTD^4$-induced bronchospasm in guinea pigs which closely resembles an asthmatic attack in man.

The compounds are accordingly indicated for therapeutic use in the treatment of diseases in which leukotrienes are implicated. These include allergic reactions of the pulmonary system in which leukotrienes are thought to be causal mediators of bronchospasm, for example, in allergic lung disorders such as extrinsic asthma and industrial asthmas such as Farmers lung and Pigeon Fanciers lung, and in other inflammatory disorders, for example, associated with acute or chronic infectious diseases such as allergic skin diseases, ectopic and atopic eczemas, psoriasis, contact hypersensitivity and angioneurotic oedema, bronchitis and cystic fibrosis and rheumatic fever. Equally important, the compounds of the invention are indicated for use in cardiovascular diseases such as shock and ischaemic heart diseases for example coronary artery disease and myocardial infarction, cerebrovascular diseases, and renal diseases for example renal ischaemia.

Thus the invention also includes a pharmaceutical composition comprising a pharmaceutically acceptable diluent or carrier in association with a pharmaceutically active compound of formula (I), or a pharmaceutically acceptable salt thereof.

The compounds may be administered by various routes, for examples by the oral or rectal route, topically or parenterally, for example by injection, and especially by inhalation, being usually employed in the form of a pharmaceutical composition. Such compositions are prepared in a manner well known in the pharmaceutical art and normally comprise at least one active compound. In making the compositions of the present invention, the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection solutions and suspensions and sterile packaged powders. For administration by inhalation, particular forms of presentation include aerosols, atomisers and vaporisers.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxybenzoate, talc, magnesium stearate and mineral oil. The compositions of the invention may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, for example, from 25 mg to 200 mg. The term "unit dosage form" refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the condition to be treated, the choice of compound to be administered and the chosen route of administration, and therefore the above dosage ranges are not intended to limit the scope of the invention in any way.

The invention is illustrated by the following Examples. The structure of the compounds prepared was confirmed by I.R. and/or n.m.r. and/or mass spectra and the purity of the product was checked in most cases by HPLC. The involatile products were examined by mass spectrometry using the fast atom bombardment (FAB) technique in the negative ion mode. Significant [M-H]$^-$ ions (and characteristic fragment ions) were observed.

EXAMPLE 1

5-{3-[2-(2-Carboxyethylthio)pentadeca-3(E)5(E)-dienyl]phenyl}-1H-tetrazole (a) 3-Cyano-cinnamyl alcohol Dimethylformamide (0.1 ml) was added to a stirred suspension of 3-cyano-cinnamic acid (30 g) in dry ether (500 ml) containing oxalyl chloride (15 ml). The mixture was stirred for 6 hours, filtered and evaporated to give the crude acid chloride as a pale solid. A solution of this acid chloride in ether (100 ml) and tetrahydrofuran (100 ml) was added to a stirred suspension of sodium borohydride-doped alumina (20 g sodium borohydride on 200 g alumina) in ether (200 ml). The mixture was stirred for 1 hour and then filtered. The filtrate was evaporated and the residue was chromatographed on silica-gel eluting with 2:1 ether:hexane to give the product as a pale oil.

(b) 3-(3-Cyanophenyl)propanol

A solution of 3-cyanocinnamyl alcohol (4.1 g) in methanol (100 ml) was hydrogenated at 50 psi over 10% palladium on charcoal (0.5 g) for 1 hour. The catalyst was filtered off and the filtrate was evaporated to give the product as a pale oil.

(c) 3-(3-Cyanophenyl)propanoic acid

A solution of 3-cyano-cinnamic acid (11.5 g) in water (200 ml) and 2M sodium hydroxide solution (35 ml) was hydrogenated at 60 psi over 10% palladium on charcoal for 1.5 hours. The catalyst was filtered off and the filtrate was acidified with 2M hydrochloric acid to precipitate the product as a white solid, m.p. 103° C.

3-(3-Cyanophenyl)propanol (alternative method)

Borane-dimethyl sulphide complex (5.8 ml) was added dropwise to a stirred solution of 3-(3-cyanophenyl)propanoic acid (9.8 g) in tetrahydrofuran (100 ml) at 15°-20° C. The solution was stirred for 2.5 hours, treated with water (5 ml) and evaporated. A solution of the residue in ether was washed successively with water, dilute sodium hydroxide solution and dilute hydrochloric acid, dried and evaporated to give the product as a pale oil.

(e) 3-(3-Cyanophenyl)propanal

Solid chromium trioxide (12.7 g) was added to a stirred solution of pyridine (20.1 ml) in dichloromethane (500 ml) at 5° C. The mixture was stirred at 5° C. for 30 minutes then Celite-Hyflo Supercel (12 g) was added, the cooling bath was removed and a solution of 3-(3-cyanophenyl)propanol (4.1 g) in dichloromethane (40 ml) was added. After stirring for a further 2 hours the dark mixture was filtered through a mixture of Fluorosil and magnesium sulphate and the filtrate was evaporated to give the product as a pale oil.

(f) 3-(3-Cyanophenyl)-1-trimethylsilyloxy-1-propene

A stirred solution of 3-(3-cyanophenyl)propanal (3.1 g), trimethylsilyl chloride (3.0 ml) and triethylamine (6.5 ml) in dimethylformamide (45 ml) was heated under reflux on an oil bath at 150°-160° C. for 4 hours. The mixture was cooled and filtered and the filtrate was diluted with hexane (200 ml) and rapidly washed successively with cold sodium bicarbonate solution, cold dilute hydrochloric acid and cold sodium bicarbonate solution again. The hexane solution was dried and evaporated and the residue was distilled under vacuum in a bulb-to-bulb apparatus to give the product as a colourless oil, b.p. 140°-150° C./0.1 mm.

(g) 3-(3-Cyanophenyl)-2-(2-methoxycarbonylethylthio)-propanal

A solution of chlorine (0.72 g) in carbon tetrachloride (10 ml) was added to a stirred solution of 3,3'-dithiobis-propanoic acid, dimethyl ester (1.9 g) in carbon tetrachloride (10 ml) at 0°-5° C. The solution was stirred for 1 hour at 0°-5° C. then evaporated without heating to give the sulphenyl chloride as a yellow oil. A solution of this sulphenyl chloride in dichloromethane (10 ml) was added to a stirred solution of 3-(3-cyanophenyl)-1-trimethylsilyloxy-1-propene (2.8 g) in dichloromethane (20 ml) at −60° to −65° C. The solution was stirred for 1 hour at −65° to −70° C. and evaporated. The residue was chromatographed on silica-gel eluting with 1:1 ether:hexane to give the product as a pale oil.

(h) 3-[2-(2-Methoxycarbonylethylthio)pentadeca-3(E),-5(E)-dienyl]benzonitrile

A 1.6M solution of n-butyl lithium in hexane (2.5 ml) was added dropwise to a stirred solution of dodeca-2-enyltriphenyl-phosphonium bromide (1.8 g) in dry tetrahydrofuran (60 ml) at −70° C. under nitrogen. The orange solution was stirred for 10 minutes at −70° C. then a solution of 3-(3-cyanophenyl)-2-(2-methoxycarbonylethylthio)propanal (0.8 g) in tetrahydrofuran (6 ml) was added and the pale solution was stirred for a further 1 hour at −70° C. then evaporated. The residue was extracted with ether and the extract was reevaporated and chromatographed on silica-gel eluting with 1:2 ether:hexane to give the product (mixed with minor amounts of the 3(Z),5(E) and 3(E)5(Z) isomers) as a pale oil.

(i) 3-[2-(2-Carboxyethylthio)pentadeca-3(E)5(E)dienyl]-benzonitrile

A solution of 3-[2-(2-methoxycarbonylethylthio)pentadeca-3(E)5(E)-dienyl]benzonitrile (396 mg) in methanol (20 ml) and 0.5M potassium carbonate solution (5 ml) was stirred at 40° C. for 5 hours. The solution was concentrated, diluted with water, acidified and extracted with ether. The extract was dried and evaporated and the residue was purified by reverse phase high pressure liquid chromatography (RPHPLC) to give the product as a pale gum.

MS (−ve ion FAB) [M-H]⁻412

NMR (300 MHz, CDCl$_3$) 2.9$\delta$ (d) (ArCH$_2$—), 3.5$\delta$ (CHS—)

(j) 5-{3-[2-(2-Carboxyethylthio)pentadeca-3(E)5(E)-dienyl]phenyl}1H-tetrazole

A stirred suspension of 3-[2-(2-carboxyethylthio)pentadeca-3(E)5(E)-dienyl]benzonitrile (285 mg), sodium azide (0.45 g) and triethylamine hydrochloride (0.95 g) in dry dimethylformamide (10 ml) was heated at 140° for 2 hours. The dark mixture was cooled and filtered and the filtrate was diluted with cold dilute hydrochloric acid and extracted with ether. The extract was dried and evaporated and the residue was purified by RPHPLC to give the product as a pale gum.

MS (−ve ion FAB) [M-H]⁻455

NMR (300 MHz CDCl$_3$/CD$_3$OD) 2.98$\delta$ (d) (ArCH$_2$—), 3.58$\delta$ (CHS—) 5.40$\delta$, 5.62$\delta$, 5.95$\delta$, 6.00$\delta$ (—CH=).

EXAMPLE 2

5-{3-[2-(2-Carboxyethylthio)pentadeca-3(Z)-enyl]-phenyl}-1H-tetrazole (a) 3-[2-(2-Methoxycarbonylethylthio)pentadeca-3(Z)-enyl]benzonitrile A 1.6M solution of n-butyl-lithium in hexane (0.45 ml) was added dropwise to a stirred solution of dodecyl-triphenylphosphonium bromide (0.37 g) in dry tetrahydrofuran (20 ml) at −70° C. under nitrogen. The yellow solution was stirred for 5 minutes at −70° C., then a solution of 3-(3-cyanophenyl)-2-(2-methoxycarbonylethylthio)-propanal (0.18 g) in dry tetrahydrofuran (4 ml) was added and the pale solution was stirred for a further 1 hour at −70° C. and then evaporated. The residue was extracted with ether and the extract was evaporated and chromatographed on silica-gel eluting with 1:2 ether:hexane to give the product as a pale oil.

(b) 3-[2-(2-Carboxyethylthio)pentadeca-3(Z)-enyl]benzonitrile

A solution of 3-[2-(2-methoxycarbonylethylthio)pentadeca-3(Z)-enyl]benzonitrile (90 mg) in methanol (6 ml) and 0.5M potassium carbonate solution (2 ml) was stirred at room temperature for 16 hours then at 40° C. for 2 hours. The solution was concentrated, diluted with water, acidified and extracted with ether. The extract was dried and evaporated and the residue was purified by RPHPLC to give the product as a pale gum.

MS (−ve ion FAB) [M-H]⁻414

NMR (80 MHz, CDCl$_3$) 2.88$\delta$ (d) (ArCH$_2$—) 3.8$\delta$ (CHS) 4.9, 5.75$\delta$ (—CH=).

(c)
5-{3-[2-(2-Carboxyethylthio)pentadeca-3(Z)-enyl]-
phenyl}-1H-tetrazole

A stirred mixture of 3-[2-(2-carboxyethylthio)pentadeca-3(Z)-enyl]benzonitrile (42.4 mg), sodium azide (65 mg) and triethylamine hydrochloride (137 mg) in dry dimethylformamide (2 ml) was heated at 130°–135° C. for 2 hours. Further sodium azide (15 mg) and triethylamine hydrochloride (30 mg) was added and the mixture was heated for a further 2 hours at 130°–135° C., cooled and filtered. The filtrate was diluted with cold dilute hydrochloric acid and extracted with ether.

The extract was evaporated and the residue was purified by RPHPLC to give the product as a pale gum.
MS (—ve ion FAB) [M-H]⁻457
NMR

EXAMPLE 3

5-{3-[2-(2-1H-Tetrazol-5-ylethylthio)pentadeca-3(E)5-(E)-dienyl]phenyl}-1H-tetrazole (a) 3-(3-Cyanophenyl)-2-(2-cyanoethylthio)propanal The sulphenyl chloride prepared from 3,3'-dithiobis-propanonitrile (0.24 g) and chlorine (0.12 g) was reacted with 3-(3-cyanophenyl)-1-trimethylsilyloxy-1-propane (0.48 g) as described in Example 1(g) to give, after chromatography, the product as a pale oil.

(b)
3-[3-(2-Cyanoethylthio)pentadeca-3(E)5(E)-dienyl]benzonitrile 3-(3-Cyanophenyl)-2-(2-cyanoethylthio)propanal (338 mg) was reacted with the ylid prepared from dodeca-2-enyltriphenylphosphonium bromide (920 mg) as described in Example 1(h). The crude product was purified by RPHPLC to give the product as a pale oil.
NMR (300 MHz, CDCl₃) 2.92δ (ArCH₂—) 3.58δ (CHS—) 5.32, 5.85, 5.94, 6.00δ (—C=).

(c)
5-{3-[2-(2-1H-Tetrazol-5-ylethylthio)pentadeca-3(E)5-(E)-dienyl]phenyl}-1H-tetrazole A stirred mixture of 3-[3-(2-cyanoethylthio)pentadeca-3(E)5(E)-dienyl]benzonitrile (103 mg), sodium azide (340 mg) and triethylamine hydrochloride (714 mg) in dry dimethylformamide (4 ml) was heated at 150°–160° C. for 4 hours. The dark mixture was worked up and the product purified as described in Example 1(j) to give the product as a pale gum.
NMR (300 MHz, CDCl₃/CD₃OD)

EXAMPLE 4

3-[2-(2-1H-Tetrazol-5-ylethylthio)pentadeca-3(E)5(E)-dienyl]benzoic acid (a) 3-(3-Methoxycarbonylphenyl)propanoic acid A solution of 3-methoxycarbonyl-cinnamic acid (15.0 g) and sodium carbonate (7.7 g) in water (200 ml) was hydrogenated at 50 psi over 10% palladium on charcoal (0.5 g) for 1.5 hours. The catalyst was filtered off and the filtrate was acidified with 2M hydrochloric acid to precipitate the product as a white solid, m.p. 81° C.

(b) 3-(3-Methoxycarbonylphenyl)propanol 3-(3-Methoxycarbonylphenyl)propanoic acid (10.5 g) was reduced with borane-dimethyl sulphide complex (5.5 ml) as described in Example 1(d) to give the product as a colourless oil.

(c) 3-(3-Methoxycarbonylphenyl)propanal 3-(3-Methoxycarbonylphenyl)propanol (1.9 g) was oxidised with chromium trioxide (5.0 g) in pyridine (7.9 ml) as described in Example 1(e) to give the product as a pale oil.

(d)
3-(3-Methoxycarbonylphenyl)-1-trimethylsilyloxy-1-propane 3-(3-Methoxycarbonylphenyl)propanal (3.9 g) was reacted with trimethylsilyl chloride (3.1 ml) in the presence of triethylamine (6.8 ml) as described in Example 1(f) to give the product as a yellow oil, b.p. 150°–160° C./0.1 mm.

(e)
3-(3-Methoxycarbonylphenyl)-2-(2-cyanoethylthio)-propanal

The sulphenyl chloride prepared from 3,3'-dithiobis-propanonitrile (0.44 g) and chlorine (0.22 g) was reacted with 3-(3-methoxycarbonylphenyl)-1-trimethylsilyloxy-1-propene (1.0 g) to give, after chromatography, the product as a pale oil.

(f)
3-[2-(2-Cyanoethylthio)pentadeca-3(E)5(E)-dienyl]benzoic acid, methyl ester 3-(3-Methoxycarbonylphenyl)-2-(2-cyanoethylthio) propanal (0.46 g) was reacted with the ylid prepared from dodeca-2-enyl-triphenylphosphonium bromide (1.1 g) as described in Example 1(h). The crude product was purified by RPHPLC to give the product as a pale oil.
MS M³⁰ 427
NMR (300 MHz, CDCl₃)

(g)
3-[2-(2-Cyanoethylthio)pentadeca-3(E)5(E)-dienyl]benzoic acid

A solution of 3-[2-(2-cyanoethylthio)pentadeca-3(E)5(E)-dienyl]benzoic acid methyl ester (80 mg) in tetrahydrofuran (2 ml) and M lithium hydroxide solution (0.4 ml) was stirred for 3 days, diluted with water, acidified and extracted with ether. The extract was dried and evaporated to give the product as a pale gum.
NMR 300 MHz (h)
3-[2-(2-1H-Tetrazol-5-ylethylthio)pentadeca-3(E)-5(E)-dienyl]benzoic acid A stirred mixture of 3-[2-(2-cyanoethylthio)pentadeca-3(E)5(E)-dienyl]benzoic acid (74.7 mg), sodium azide (119 mg) and triethylamine hydrochloride (247 mg) in dry dimethylformamide (3 ml) was heated at 150°–160° C. for 4 hours. Further sodium azide (120 mg) and triethylamine hydrochloride (240 mg) were added and the mixture was heated for a further 4 hours, then worked up as described in Example 1(j) to give the product as a pale gum.

NMR (300 MHz, CDCl$_3$/CD$_3$OD) 2.9$\delta$ (ArCH$_2$—) 5.36, 5.64, 5.95, 6.00$\delta$ (—CH=)

The active compounds of the invention are preferably employed in salt form. The following formulations are given by way of example:

EXAMPLE 5

Soft gelatin capsule

Each soft gelatin capsule contains:
Active ingredient: 150 mg
Arachis Oil: 150 mg After mixing together, the blend is filled into soft gelatin capsules using the appropriate equipment.

EXAMPLE 6

Hard gelatin capsule

Each capsule contains:
Active ingredient: 50 mg
PEG 4000: 250 mg

The PEG 4000 is melted and mixed with the active ingredient. Whilst still molten the mixture is filled into capsule shells and allowed to cool.

EXAMPLE 7

Aerosol

Active ingredient: 10 mg
Ethanol: 50 mg
Dichlorodifluoromethane (Propellant 12): 658 mg
Dichlorotetrafluoroethane (Propellant 114): 282 mg The active ingredient is dissolved in the ethanol. The concentrate is filled into extruded aluminium cans for inhalation aerosols. The cans are degassed with propellant 12 and sealed with an appropriate metered dose valve. The volume of product expelled per actuation is 50 of 100 $\mu$l equivalent to 0.5–1 mg active ingredient.

We claim:

1. A compound of the formula

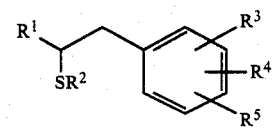

in which $R^1$ is an alkenyl group containing 10 to 15 carbon atoms, $R^2$ is of the formula —(CH$_2$)$_x$R$^{12}$ where x is 1 to 5 and $R^{12}$ is carboxyl, nitrile, CONR$_2^7$ wherein each $R^7$ is hydrogen or C$_{1-4}$ alkyl or 5-tetrazolyl, $R^3$ is nitrile, CONR$_2^7$ wherein each $R^7$ is hydrogen or C$_{1-4}$ alkyl, 5-tetrazolyl or carboxyl and $R^4$ and $R^5$ are hydrogen, with the proviso at least one of $R^{12}$ and $R^3$ is always 5-tetrazolyl, or a pharmaceutically acceptable salt thereof.

2. 5-{3-[2-(2-Carboxyethylthio)pentadeca-3(E)-5(E)-dienyl]phenyl}-1H-tetrazole.

3. A pharmaceutical formulation comprising a compound according to claim 1 in unprotected form, or a pharmaceutically acceptable salt thereof, in admixture with a pharmaceutically acceptable diluent or carrier therefor.

4. A method of treating a mammal, including a human, suffering from, or susceptible to, an allergic disorder, which comprises administering to the mammal an effective amount of a compound according to claim 1 in unprotected form, or pharmaceutically acceptable salt thereof.

* * * * *